United States Patent [19]

Lynn et al.

[11] Patent Number: 5,013,667
[45] Date of Patent: May 7, 1991

[54] APPARATUS AND METHOD FOR MEASURING HALOGEN CONTENT

[75] Inventors: Theodore R. Lynn, Hamden; Stephen R. Finch, Seymour, both of Conn.

[73] Assignee: Dexsil Corporation, Hamden, Conn.

[21] Appl. No.: 563,939

[22] Filed: Aug. 6, 1990

Related U.S. Application Data

[63] Continuation of Ser. No. 59,560, Jun. 8, 1987, abandoned.

[51] Int. Cl.⁵ .............................................. G01N 33/00
[52] U.S. Cl. ...................................... 436/126; 436/60; 436/140; 436/165; 422/61
[58] Field of Search .................................. 436/39-41, 436/60, 61, 124, 125, 126, 140, 164, 165; 422/58-61; 210/909; 208/262; 222/94, 541

[56] References Cited

U.S. PATENT DOCUMENTS

3,068,855 12/1962 Furlong .................................. 422/58
3,498,751 3/1970 Newhart et al. ....................... 436/60
4,686,192 8/1987 Fisher ................................... 436/60

Primary Examiner—Thomas Wallen
Attorney, Agent, or Firm—Victor E. Libert

[57] ABSTRACT

An apparatus, which may be embodied in a disposable field test kit, and a test method serves to measure the halogen (bromine, chlorine, iodine) content, especially the chlorine content, of hydrocarbon liquids. The apparatus includes a sampling device in which a quantity of the hydrocarbon liquid, such as a used oil, is suctioned into a frangible collector such as a capillary tube to control sample size, and the tube is deposited into a flexible container which also contains frangible ampules holding pre-measured quantities of reagents, including a solvent for the sample. The container is squeezed to break the tube and ampules to release their contents in prescribed order. The sample is first solvated, then reacted with an alkali metal reagent which will form halides from halogen material present, extracted into an aqueous phase, titrated, and contacted with a color change indicator which acquires a characteristic color dependent upon the halogen material content.

17 Claims, 1 Drawing Sheet

APPARATUS AND METHOD FOR MEASURING HALOGEN CONTENT

This is a continuation of copending application Ser. No. 07/059,560, filed on June 8, 1987, now abandoned.

BACKGROUND OF THE INVENTION

1. Field of the Invention

The present invention is concerned with a method and apparatus for measuring the halogen content of hydrocarbon liquids, including used or waste materials as well as new or virgin materials, for example, used or virgin lubricating crankcase, hydraulic and furnace oils and metal working fluids. More particularly, the present invention is concerned with a measuring method and apparatus of the type described which are particularly well suited for field testing.

DESCRIPTION OF RELATED ART AND PROBLEMS ENCOUNTERED IN THE FIELD OF THE INVENTION

2. Related Art

Co-pending patent application Ser. No. 529,154 of David J. Fisher, which issued as U.S. Pat. No. 4,686,192 on Aug. 11, 1987, discloses a chemical test kit and method for detecting impurities in an oil sample which is placed within a test tube-shaped resilient container in which are disposed reagent-containing breakable ampules. The ampules are broken within the resilient container in a specified sequence by squeezing the container from the outside. The method of the Fisher disclosure includes reacting the oil sample with an alkali metal, by breaking an ampule of the latter and then adding an aqueous buffer/acid solution which is separated from the oil layer and transferred to a second resilient container in which first a mercury titrant-containing ampule and then a dye indicator-containing ampule are broken, in order to indicate by a color change the level of halogen content of the oil sample.

U.S. Pat. No. 3,068,855 issued Dec. 18, 1962 to N. B. Furlong, Jr. discloses a disposable blood gas analyzer comprising a hypodermic needle syringe fitted with an evacuated capsule contained within a reaction chamber. The glass capsule has a thin-walled, shear end supported within the base of the hypodermic needle at the neck portion of the reaction chamber. Upon injection of the hypodermic needle into the vein of the patient and flexing of the syringe to rupture the shear end of the vacuum capsule, the patient's blood pressure forces blood into the evacuated ampule which is then crushed to release the measured quantity of blood for analysis.

PROBLEMS ENCOUNTERED IN THE FIELD OF THE INVENTION

Environmental protection laws and regulations of the Federal Environmental Protection Agency require that any waste oil containing more than a prescribed quantity of chlorine must be classified as a hazardous waste, and becomes subject to strict requirements concerning its storage and disposal. Currently, the prescribed quantity is 1,000 parts by weight chlorine per million parts by weight of chlorine-containing oil. It is therefore necessary to determine the chlorine content of waste oils or other hydrocarbon liquids and to determine if they contain more or less than the specified level of chlorine which would constitute them as hazardous wastes. For obvious reasons of time and economy, it is desirable to be able to field-test the chlorine content of hydrocarbon liquids at points of use, shipment and/or disposal. Further, the test for chlorine level is suitably carried out by a test for halogens generally. A field test which determines whether or not the chlorine content of a transformer oil exceeds a certain level, and field test kits for carrying out such tests, are known, as shown by the above-mentioned Fisher Patent Application. This application describes test kits for testing the polychlorinated biphenyl (PCB) content of transformer oils; such kits are commercially available are suitable for use by relatively untrained persons.

The testing of hydrocarbon liquids, particularly oils such as lubricating, hydraulic, and crankcase oils and the like, presents problems in obtaining a precisely measured sample and accurate analysis. These problems are exacerbated by conditions encountered in field testing, such as the use of less trained personnel and varying conditions, e.g., low temperatures resulting in increased viscosity as encountered in taking samples from waste oil or other hydrocarbon liquids stored outdoors or in unheated and uncooled structures. Another difficulty is the possibility of interference with the analytical chemical reactions caused by additives or contaminants in the hydrocarbon liquid. Used oils often contain contaminants such as lead, iron or other metals; sulfide contaminants are often found in waste lubricating oils.

When the sample is taken by introducing a prescribed number of drops into the test apparatus, e.g., from an eyedropper or pipette, the size of the drops varies with the temperature of the oil and the resultant variations in sample size adversely affect the accuracy of the analysis. At very low temperatures, it is often difficult to form and discharge drops of viscous oils. Even if a measured volume device, such as a graduated syringe or the like is used to draw a sample, a pre-measured volume of which is then discharged from the device into the test apparatus, it is difficult to accurately read the volume markings on the sampling device because the oil coats and opacifies it, especially if there is an initial over-fill. This problem is exacerbated in the case of dirty, used oils. Further, upon discharge of the oil sample from a volume-calibrated device, the quantity discharged is lessened by the amount of oil which coats the sampling device, thereby adversely affecting accuracy and reproducibility of the test.

SUMMARY OF THE INVENTION

In accordance with the present invention there is provided an apparatus for testing liquids, e.g., hydrocarbon liquids such as used and virgin oils. The apparatus comprises a sampling means and a reaction container system comprising at least a first container. The sampling means comprises (i) a frangible collector, e.g., a frangible capillary tube, of pre-determined interior volume which has a sampling end and a suction end, (ii) a suction means (e.g., a syringe) having a suction port, and (iii) a coupling means releasably connecting the suction end of the collector in flow communication with the suction port. With this construction, suction applied to the collector while the sampling end thereof is immersed in the hydrocarbon liquid will fill the collector with the liquid and retain it therein. The first container has an opening therein and is dimensioned and configured to have the entire collector, e.g., the capillary tube, containing the sample deposited within the first container from exteriorly thereof; at least a portion of the first container is sufficiently flexible to enable breaking of the collector within the first container by squeezing the first container from the exterior thereof.

In accordance with another aspect of the present invention, there is provided a method for measuring the halogen content or at least detecting a threshold halogen content of a hydrocarbon liquid, e.g., an oil, the method comprising the following steps. A measured quantity sample of the hydrocarbon liquid is taken by suctioning the liquid into a frangible collector, e.g., a frangible capillary tube having a pre-determined interior volume, e.g., completely filling the capillary tube. The collector containing the sample is deposited into a container from exteriorly thereof and is broken within the container to release the liquid from the collector. The liquid sample is then contacted with one or more reagents to provide a reaction residue within the container, the quantity and type of reagents being selected to provide, in conjunction with the measured quantity of liquid sample, a detectable indication, e.g., a visually detectable indication, of the halogen content of the liquid. The visually detectable indication may be a characteristic color.

In accordance with one aspect of the invention, the method includes contacting the liquid hydrocarbon sample with an alkali metal reagent to react the alkali metal reagent with any halogen materials in the sample in order to form inorganic halides therefrom. The resultant reacted sample is contacted with an aqueous extractant which extracts the resultant inorganic halides and forms an aqueous phase which separates from a hydrocarbon phase. The inorganic halides in the aqueous phase are titrated with a pre-measured quantity of a titrant, and the titrated aqueous phase material is then contacted with an indicator which acquires a characteristic color depending upon whether the quantity of inorganic halides present in the aqueous phase is sufficient to react with all of the added titrant. In this manner, the resultant color indicates whether a pre-selected level of halogen was present in the liquid hydrocarbon sample. By simply changing the pre-selected quantity of titrant, for example, the quantity supplied with a field test kit, different levels of halide can be selected for the color change point.

The invention also provides for solvating the hydrocarbon liquid by dissolving it in a suitable solvent to provide a reaction medium which enhances the reaction with the alkali metal reagent and facilitates subsequent phase separation of the hydrocarbon residue and the aqueous phase extractant. In accordance with another aspect of the invention, the solvent may comprise an ether selected from the group consisting of one or more of butyl ether, n-amylether, isoamylether, diethylene glycol dimethyl ether, diethylene glycol diethyl ether and diethylene glycol dibutyl ether. The solvent may also include one or both of an aromatic solvent and an aliphatic solvent.

Reference in the specification and claims to the "halogen content" of a hydrocarbon liquid or to "halogen material" contained in a hydrocarbon liquid means and includes halide compounds, such as organohalides, e.g., polychlorinated biphenyls ("PCBs"), inorganic halides, e.g., sodium chloride, and halogen or halide gases which may be dissolved in the liquids.

Terms such as "No. 2 fuel oil", "No. 6 fuel oil", "petroleum ether", and "mineral spirits" have their usual, accepted meanings in the petroleum and petrochemical fields. Reference in this regard is made to the *Chemical Engineers' Handbook*, edited by John H. Perry, Third Edition (Textbook Edition), 1950, McGraw-Hill Book Company, Inc., New York, N.Y., and *The Condensed Chemical Dictionary*, Tenth Edition, 1981, Revised by Gessner G. Hawley, Van Nostrand Reinhold Company, New York, N.Y. Pertinent disclosures of these references (e.g., page 156 of *Chemical Engineers' Handbook* and pages 712–713 of *The Condensed Chemical Dictionary*) are incorporated by reference herein.

DETAILED DESCRIPTION OF THE INVENTION AND PREFERRED EMBODIMENTS THEREOF

The method of the present invention includes taking a pre-measured sample, as described in detail below, of a hydrocarbon liquid and contacting the sample liquid with an alkali metal reagent. A solvent may be used to dissolve the sample in order to provide a medium which facilitates both (1) reaction of the halogen content of the sample with the alkali metal reagent to form alkali metal halides, i.e., inorganic halides and (2) complete or nearly complete separation of the resultant inorganic halides from the solvated sample. The latter step is accomplished by contacting the reacted hydrocarbon sample with an aqueous phase extractant to dissolve the inorganic halide in the extractant. A clean phase separation of the solvated hydrocarbon liquid residue and the aqueous phase having the inorganic halide dissolved therein enables a more complete recovery of the inorganic halides and concomitantly greater accuracy in determining the halogen content of the hydrocarbon liquid. This determination is made by titrating the separated aqueous phase for its halide content; any halides remaining in the hydrocarbon phase will not be accounted for by the titration. Certain solvents, as described in more detail below, are preferred because of their ability to facilitate both the reaction to form inorganic halides and the phase separation with a variety of hydrocarbons, including heavy hydrocarbon liquids such as asphaltic-derived No. 6 fuel oil.

Figure 1:
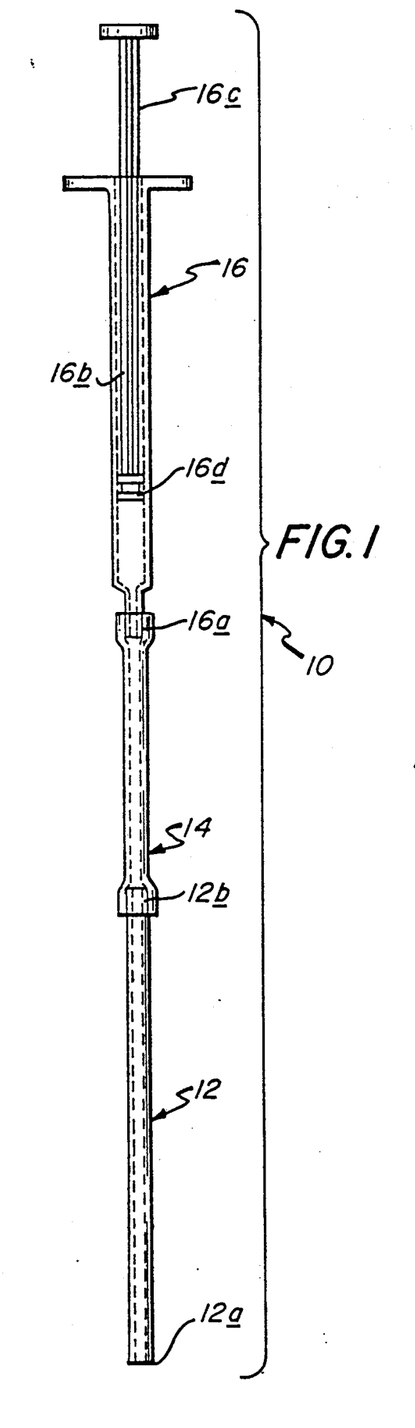
FIG. 1 is an elevation view of one embodiment of a sampling means forming a part of the apparatus of the present invention.

A suitable apparatus in accordance with an embodiment of the invention is shown in the drawings, FIG. 1 of which shows a sampling means generally indicated at 10 and comprised of a combination which includes a collector comprising a frangible capillary tube 12, the free end of which comprises sampling end 12a and the opposite end of which comprises suction end 12b. Capillary tube 12 is of a controlled, pre-determined length and inside diameter, so that, when completely filled with a hydrocarbon liquid sample, e.g., an oil sample, it holds an accurately pre-determined sample quantity of the oil or the like. Suction end 12b of capillary tube 12 is releasably but snugly inserted within one end of a coupling means 14 which comprises, in the illustrated embodiment, a length of flexible rubber or plastic tubing. The opposite end of coupling means 14 has snugly inserted therein the suction port 16a of a suction means 16 which, in the illustrated embodiment, comprises a needleless, conventional hypodermic syringe. Suction means 16 thus includes a main or body portion 16b of cylindrical, tubular configuration within which is received a plunger 16c having a flexible plunger seal 16d affixed to the end thereof which travels through body portion 16b. Body portion 16b may contain thereon the usual volume indicia (not shown), but such indicia on the suction means are not necessary to the practice of the present invention.

The sampling means illustrated in FIG. 1 may be utilized to draw a precisely measured quantity of sample oil, regardless of opacity and contamination of the sample, and without variation in the quantity drawn caused by different viscosities of a given oil sample. The sampling device of the invention provides a means for positively filling a pre-selected volume of collector, e.g., the capillary tube 12 of the illustrated embodiment, the entirety of which can be conveniently deposited into any suitable container for testing of the oil sample. Once the capillary tube is filled with the oil sample, suction maintained on suction end 12b of capillary tube 12 maintains the tube filled without loss of sample while the filled tube is moved from the receptacle from which the sample was drawn to the reaction container into which the sample is to be deposited. Suction is maintained simply by leaving plunger 16c undisturbed in place when capillary tube 12 is completely filled with the sample.

The sampling procedure described avoids entirely the loss of an indeterminate portion of the sample due to coating by the oil of a sampling device (such as a pipette) into which the oil is drawn and from which a pre-selected volume of sample is discharged into the reaction container. The procedure also avoids variations in sample size inherent in drop-wise addition of a selected number of drops of sample to the reaction container. For example, an eyedropper method which depends upon the formation of drops from an eyedropper to control the size of the sample transferred to the reaction container, the size of individual drops will vary widely depending on factors such as the viscosity of the particular sample being taken.

The sample is taken by dipping sampling end 12a of capillary tube 12 into the body of oil from which the sample is to be taken, which body of oil may be contained in any suitable container such as an open trough, a 55-gallon drum or the like. If necessary, a portion of the oil can be poured or drawn from its storage container into any convenient small receptacle such as a cup, and capillary tube 12 dipped into the withdrawn sample with the plunger 16c pushed fully in to the stop provided by suction port 16a. Plunger 16c is then raised a distance sufficient to draw the desired size sample into the capillary tube 12. Although a volume fill mark may be provided on tube 12, it is preferred to entirely fill capillary tube 12 with the oil sample. The sample size is thus conveniently selected by using an appropriately sized capillary tube. Coupling means 14, which is conveniently provided by a short length of flexible tubing, is preferably made of a transparent or translucent plastic tubing so that the operator can readily see the level of the oil sample within capillary tube 12 in order to completely fill the tube but not to overfill it so as to draw oil sample into the tubing of coupling means 14. However, even if the operator should over-fill and draw some oil into coupling means 14, most or all of the excess oil (oil in addition to the volume of oil needed to completely fill capillary tube 12) will not accompany the capillary tube 12 when the latter is detached from coupling means 14 as described below. When the capillary tube 12 is filled with the desired amount of sample, e.g., is completely filled with the oil, plunger 16c is left in place to insure that no oil flows out of the capillary tube 12 when it is withdrawn from the body of sampled oil for transfer to a suitable reaction container system. The exterior of capillary tube 12 may be wiped clean, e.g., with a piece of absorbent tissue paper, to thereby remove from it oil coating the immersed portion of the outside of the capillary tube 12. This removes such coated oil, which is in excess of the measured quantity provided by completely filling the interior of the capillary tube 12. Any suitable frangible collector capable of retaining, without loss, the measured sample during transfer of the collector to a container may be used. However, a frangible capillary tube such as tube 12 is preferred because by merely maintaining suction on the suction end of the tube the entire sample is retained therein without loss during cleaning of excess sample from the exterior of the capillary tube, and transfer of the tube to the container. Further, the tube shape is ideally suited for depositing the tube and its content of sample into a relatively small opening of the first container, as described below.

Figure 2:
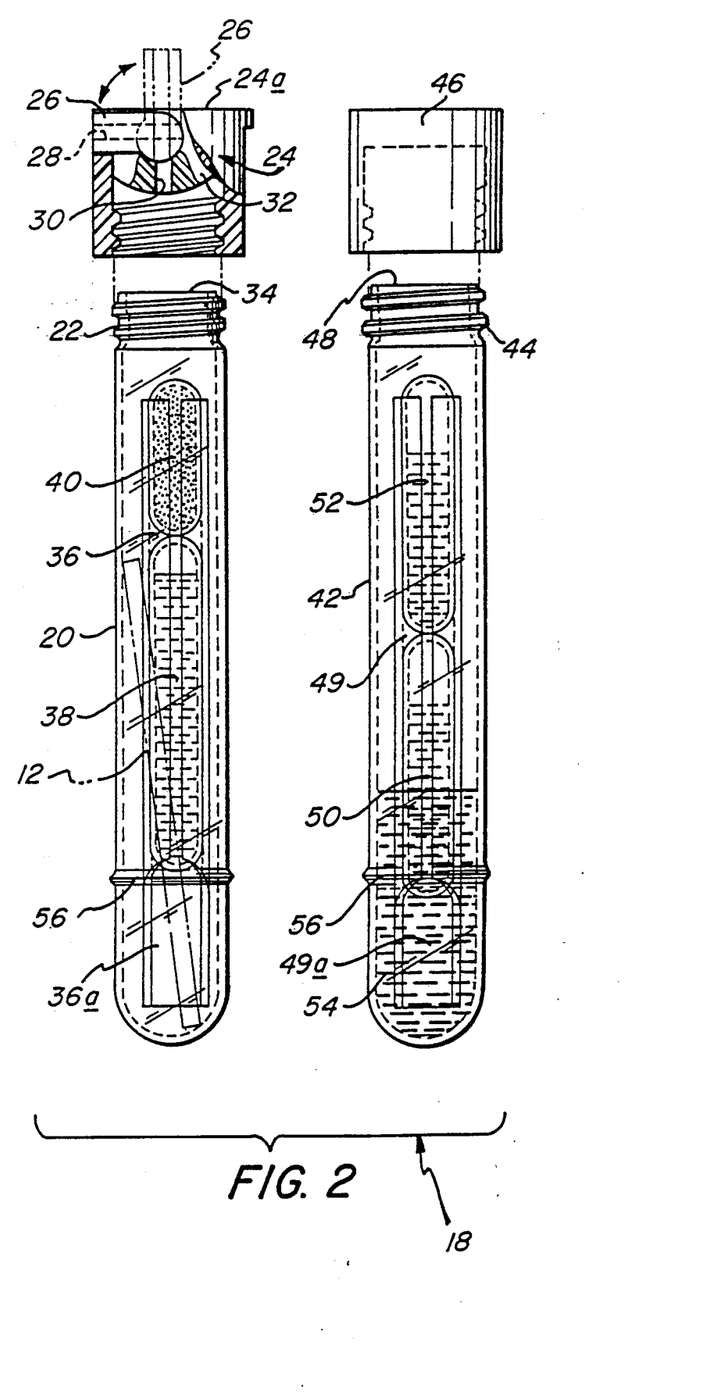
FIG. 2 is an exploded elevation view, partially in cross-section, of a reaction container system comprising first and second containers, the combination of which with the sampling means of FIG. 1 comprises one embodiment of the apparatus of the present invention.

Referring now to FIG. 2, a reaction container system is generally shown at 18 and comprises a first reaction container 20 and a second reaction container 42, each of the first and second containers comprising a thin-walled, resilient container having the overall configuration of a test tube. The first and second containers are both made of a transparent or semi-transparent material, such as a clear or nearly clear synthetic organic polymeric material, i.e., a plastic such as polyethylene. In a thin-wall configuration, polyethylene is sufficiently transparent to observe color changes through the first and second containers.

First container 20 has a screw-threaded top 22 which is dimensioned and configured to have screwed thereon a first closure means 24 which comprises a screw cap having flat base surface 24a and a pivotable spigot 26 mounted thereon for pivoting movement between a closed position, and an open position. The closed position is illustrated in solid line rendition in FIG. 2, in which a spigot conduit 28, which extends through spigot 26, is isolated from a cap conduit 30 which extends through a hemispherical base portion 32 of first closure means 24. Spigot 26 is dimensioned and configured to form part of, or be recessed within, flat surface 24a when spigot 26 is in its closed position. Pivotable spigot 26 is pivotable to the open position, shown in dash outline in FIG. 2, in which spigot conduit 28 is aligned in liquid flow communication with cap conduit 30. When in the open position, spigot 26 permits discharge of liquid from first reaction container 20 with first closure means 24 threaded onto screw threaded top 22 to close the opening 34. When spigot 26 is in the closed position, the contents of first container 20 are sealed by first closure means 24.

An ampule support 36 comprises a longitudinally split and shaped tube of stiff but flexible plastic material within which a first ampule 38 and a second ampule 40 are retained. Ampules 38 and 40 have a diameter somewhat greater than the inside diameter of the tube from which ampule support 36 is fashioned so that the elastic resiliency of support 36 causes the split tube to firmly grip the first and second ampules therewithin. Ampule support 36 has a support portion 36a which is formed by cutting away about half the circumference of the tube from which ampule support 36 is fashioned. Support portion 36a is seated in the bottom of first reaction container 20.

Second container 42 is similar or identical in construction to first container 20 and has a screw-threaded top 44 dimensioned and configured to receive thereon a second closure means 46 which, in the illustrated embodiment, is comprised of a simple screw cap which serves to close opening 48 of second container 42. An ampule support means 49, similar or identical in construction to ampule support means 36, is contained within second container 42 and supports therein a third ampule 50 and a fourth ampule 52. Like ampule support 36, ampule support 49 has a support portion 49a which is seated at the bottom of second container 42.

Second container 42 contains a quantity of an aqueous extractant liquid, indicated at 54, which occupies only a minor portion of second container 42. Typically, 7 milliliters of liquid 54 might be provided in a container of 25 or 30 milliliters capacity.

First ampule 38 contains a measured quantity of a suitable solvent for hydrocarbon liquids, such as isooctane, an oxygenated solvent such as an ether, or a mixture of an ether and an aliphatic and/or an aromatic solvent. It also contains a catalytic agent such as napthalene and diethylene glycol dimethyl ether. A second ampule 40 contains a pre-measured quantity of alkali metal reactant such as sodium biphenyl, sodium naphthalene, or an elemental alkali metal such as lithium or sodium in fine particulate form. If elemental alkali metal is used, it is usually packaged within second ampule 40 in a halogen-free, light base oil such as mineral oil. Third ampule 50 contains an accurately pre-measured quantity of a titrant and fourth ampule 52 contains a pre-measured quantity of a color indicator.

A volume indicia 56 is formed near the lower (as viewed in FIG. 2) portion of second container 42 to indicate a pre-selected volume, for example, a 5 milliliter volume, of second container 42. This volume indicator serves a purpose as described below in the analysis to be carried out using the apparatus of the invention. In the illustrated embodiment, a fill line indicia is not needed for first container 20. However, in order to avoid the necessity of procuring and stocking two types of containers for the reaction container system, the identical type or model of container may be used for both the first and second containers. Accordingly, in the illustrated embodiment, first reaction container 20 has the identical fill mark (volume indicia 56) thereon although it is not needed for utilization of the apparatus in accordance with the present invention.

In order to facilitate handling of the components of the apparatus, the entire kit, comprising sampling means 10 and reaction container system 18 together with a tissue wipe (not shown) for cleaning the exterior of tube 12, may conveniently be packaged in a disposable cardboard container formed to have spaced-apart circular perforations which are sized to receive, respectively, the first and second containers and removably hold them in a side-by-side upright position as illustrated in FIG. 2, like a pair of test tubes in a test tube rack. For this purpose, the container may be formed with an extension flap folded and fastened into a box channel in which the perforations are formed.

In operation, after filling capillary tube 12 as described above with a sample of the hydrocarbon liquid, e.g., oil, to be tested, and wiping off any excess oil on the exterior surface of capillary tube 12, first closure means 24 is unscrewed from first reaction container 20 and capillary tube 12 is detached from coupling means 14 and dropped into first reaction container 20. The filled capillary tube 12 is shown in dash lines in FIG. 2 as deposited within first reaction container 20.

This is accomplished by holding capillary tube 12 above the opening 34 of first container 20, and pulling the capillary tube 12 free of coupling means 14 and dropping it into container 20. Releasing capillary tube 12 from the flexible tube comprising coupling means 14 may be facilitated by pinching the flexible tube between thumb and forefinger immediately above capillary tube 12. First closure means 24 is then screwed back into place with capillary tube 12 and its oil content within first container 20 as illustrated by dash outline in FIG. 2. By pinching the flexible tube of coupling means 14 at the top of capillary tube 12, any excess oil inadvertently drawn into the coupling means 14 is prevented from draining into first container 20. Thus, the sample size is precisely controlled at the volume provided by the volume of the capillary tube 12.

The sides of first container 20 are squeezed to pinch them together and crush therewithin the capillary tube 12, care being taken not to break either of the ampules 38, 40 at this time. The resilient construction of container 20 causes it to regain its shape after the squeezing pressure is relaxed. Crushing of the frangible capillary tube 12 insures that all of the oil sample contained therein is rendered fully accessible to the reagents in the following steps of the test procedure.

With first closure means 24 firmly in place and its pivotable spigot 26 positioned in its closed position illustrated in solid lines in FIG. 2, first ampule 38 is then crushed by squeezing first reaction container 20 in the vicinity of the ampule 38 to release the solvent it contains. First reaction container 20 is then shaken vigorously, say for about 30 seconds, in order to thoroughly mix the solvent and the oil sample. Second ampule 40 is now crushed by squeezing first container 20 in the vicinity of ampule 40 to release the alkali metal reagent it contains. First container 20 is then gain shaken thoroughly for a period of time, say 10 seconds. The alkali metal reagent, e.g., metallic sodium, will react with halogen materials in the solvated oil, such as with chlorinated hydrocarbon compounds, to form sodium halides, e.g., sodium chloride. In this manner, organic chlorides contained in the oil are converted to an equivalent quantity of inorganic halide compounds, e.g., sodium chloride. The alkali metal reactant may be provided as an elemental alkali metal, usually as a powder in a suitable carrier such as mineral oil, or as one or more suitable organometallic compounds of alkali metals. For example, metallic sodium or lithium may be used, or sodium biphenyl or sodium naphthalene.

At this stage of the test procedure, first closure means 24 is unscrewed from first container 20 and second closure means 46 is unscrewed from second container 42. The extractant liquid 54 is poured from second container 42 into first container 20 and first closure means 24 is then screwed tightly into place on first container 20. Container 20 is then shaken vigorously for about 10 seconds and vented by partially unscrewing first closure means 24. Closure means 24 is then retightened and container 20 again shaken vigorously for an additional period of time, say 10 seconds. The venting is repeated, closure means 24 is again retightened, after which first reaction container 20 is positioned upside down (with opening 34 at the bottom) by placing the flat surface 24a of closure means 24 on any convenient flat surface. First container 20 is left undisturbed for at least about two minutes in order to allow the separation of an aqueous phase and the hydrocarbon or oil phase, and second closure means 46 is removed from second container 42. The extractant liquid may comprise an aqueous solution containing sodium sulfate, sulfuric acid, monosodium phosphate and cadmium sulfate. The sodium sulfate serves as an emulsion breaker so that if the hydrocarbon liquid sample tested contains high concentrations of surfactants as do some hydrocarbon fuels, the tendency of the surfactants to form emulsions is overcome and a clean separation of the admixed hydrocarbon liquid sample and extractant liquid 54 into respective aqueous and hydrocarbon phases is obtained. The sulfuric acid content of the liquid extractant 54 is sufficient to neutralize any unreacted metallic sodium and, in combination with the monosodium phosphate, provide a sodium acid phosphate buffer to maintain a pH level appropriate for carrying out the analytical determination. The cadmium sulfate serves to react with sulfur compounds, e.g., bisulfides and sulfides, which may be present in the test sample and, if unreacted, might interfere with the analytical determination.

After the oil and aqueous phases are fully separated by the oil phase rising to the top of the liquid within container 20 to leave the aqueous phase below the oil phase and in contact with first closure means 24, container 20 is gently picked up while being maintained in an upside down position with closure means 24 pointed downwardly, and positioned above opening 48 of second container 42. Pivotable spigot 26 is then moved to its open position (illustrated in dash lines in FIG. 2) and the sides of first container 20 are gently squeezed to dispense into second container 42, up to the fill line indicia 56 thereof, a quantity of the separated aqueous phase. With this precisely measured (by indicia 56) quantity, say 5 milliliters, of the aqueous phase material thus placed within second container 42, second closure means 46 is screwed tightly onto second reaction container 42 to seal it. Third ampule 50, which contains a pre-measured quantity of a mercuric nitrate titrant, is then crushed within second container 42 by pinching second container 42 from the outside in the manner as described above, and reaction container 42 is vigorously shaken for about 10 seconds to thoroughly mix the reactants.

Fourth ampule 52, which contains a color change indicator such as diphenyl carbazone or a combination of diphenyl carbazone and bromphenyl blue, is then similarly crushed from the exterior of container 42 by pinching the latter, and the contents shaken for an additional 10 seconds. A distinctive color or color change is provided by the indicator material depending on whether or not the amount of halide present was greater or less than the equivalent titrant. For example, inorganic chlorides formed by reaction of the alkali metal reagent with the chlorine material content of the sample react with the mercuric nitrate titant to form mercuric chloride. If the amount of chloride ions in the aqueous phase is insufficient to consume all the mercuric ions, excess mercuric ions react with the diphenyl carbazone dye indicator to provide a characteristic blue or blue-violet color. On the other hand, if the amount of chloride ions is sufficient to react with all the mercuric ions, the reaction residue remains colorless or has a yellowish cast. Thus, by pre-selecting the amount of titrant and the sample size of the hydrocarbon liquid, the color change point may be selected at any desired level of chlorine material content of the hydrocarbon to be tested. The foregoing discussion applies equally to bromine and iodine materials, although it will be appreciated that chlorinated hydrocarbons are of primary environmental concern. For example, the present invention enables accurate field detecting of threshold levels of polychlorinated biphenyls and other organochloride compounds in hydrocarbon liquids. The pre-encapsulated reagent quantities are carefully controlled, and the sampling means 10 permits the taking of a precisely controlled quantity of sample hydrocarbon liquid so that, as confirmed by the data reported below, accurate, reproducible test results are obtained.

It has been found to be advantageous to dilute the hydrocarbon liquid sample to be analyzed with a solvent, particularly in the case of highly viscous and/or heavily contaminated hydrocarbon liquids such as No. 6 fuel oil or used crankcase oils contaminated with combustion waste products. Generally, aliphatic solvents are preferred over aromatic solvents because of health hazards associated with aromatics, and their tendency to emulsify the hydrocarbon samples. Such emulsification prevents or makes more difficult a clean phase separation between the aqueous extractant and the hydrocarbon sample as is needed to facilitate as complete as possible recovery into the aqueous phase of the inorganic halides formed by the alkali metal reagent. Dodecylbenzene does not have such emulsion-forming tendencies and it, as well as other aromatics such as benzene, toluene and xylenes may, if mixed with other solvents, be useable as part of a solvent blend in the practice of the invention. However, aliphatic solvents are preferred and normally liquid aliphatic solvents, e.g., aliphatic solvents of octane or higher molecular weight, are preferred to those of lower molecular weight because of the high flamability of the latter. Pentane, hexane and isooctane, as well as ethylacetate, pristane, heptamethylnonane and propylene tetramer have been employed as solvents.

With some No. 6 fuel oils, particularly those derived from higher boiling or asphaltic feed stocks, less than complete chloride recovery was attained with, e.g., aliphatic solvents, with the result that the indicated threshold level of chloride ion was lower than the actual chloride content of the sample. It has been found that oxygenated solvents, such as esters and ethers, have certain advantages including the ability to provide more complete reaction of the halide content of heavy hydrocarbon liquids such as No. 6 fuel oil. Esters could undergo hydrolysis during alkaline conditions which might exist if excess alkali metal is present to react with buffer ingredients in the aqueous extractant. Ethers are not subject to such hydrolysis and are accordingly preferred to esters. Suitable ethers for use as solvents, either alone or in a mixture with other solvents, especially aliphatic solvents, include butyl ether, pentyl ether, isoamyl ether, diethylene glycol dimethyl ether (sometimes called diglyme or diglycol methyl ether), diethylene glycol diethyl ether and diethylene glycol dibutyl ether. Diethylene glycol diethyl ether is advantageous because of its high flash point compared to the other ether solvents and concomitant safety in handling, and its commercial availability at reasonable cost. Thus, the solvent may comprise a mixture of (a) diethylene glycol dibutyl ether and (b) diethylene glycol diethyl ether, e.g., from about 5 to 25 volume percent of (a) and from about 95 to 75 volume percent of (b). Optionally, naphthalene may be added to the foregoing mixture, in an amount of about 5% to 20% by weight of the total weight of the solvent mixture.

Generally, a weight ratio of solvent to hydrocarbon liquid sample of from about 0.65 to 4, e.g., about 1 to 1.5 or 2, has been found to be useful in preparing the sample for the analytical reactions employed in the method of the invention.

The repeatability of the size of an oil sample taken by, respectively, two drop-count techniques and the capillary tube technique of the present invention was tested, as follows.

CASE 1. DROP COUNT FROM A PIPETTE

A blow-molded plastic pipette having a nominal orifice inside diameter of 1.9-2.1 mm was used to draw a sample of used crankcase oil and five drops of the oil were deposited from the pipette into a receptacle and weighed on an analytical balance. A total of 6 samples were so taken and showed a mean weight of 0.1135 grams ±10.2%.

CASE 2. DROP COUNT FROM A PLASTIC CAPILLARY TUBE

The pipette used in Case 1 was fitted with a plastic capillary tube having a nominal orifice inside diameter of 1.6 mm. Five drops of the oil were deposited from the pipette through the capillary tube into a receptacle and weighed on the same scale as used in Case 1. A total of 4 samples were so taken and showed a mean weight of 0.09633 grams ±5.0%.

CASE 3. FILLED CAPILLARY TUBE SAMPLING IN ACCORDANCE WITH THE METHOD OF THE PRESENT INVENTION

A glass capillary tube 102 mm long and of nominal 23 mm inside diameter was weighed empty, and then was suction-filled with oil by using the capillary tube in a sampling device as illustrated in FIG. 1. The filled capillary tube was deposited in a receptacle and weighed to obtain the weight of the sample. A total of 12 samples of oil so weighed showed a mean weight of 0.3746 grams, ±2.54%.

The results of Cases 1, 2 and 3 show that the technique of Case 3 provides better repeatability than either of the drop count techniques used. It should be noted that in Cases 1 and 2, repeated use was made of the same sampling device whereas in Case 3 a fresh capillary tube was used each time. Therefore, the test in Case 3 actually shows a reproducibility which is markedly better than the mere repeatability of Case 1 or Case 2.

In order to demonstrate the efficacy of a field test kit comprising one embodiment of the present invention, samples of hydrocarbon fluids were contaminated with known quantities of chlorine compounds and tested with the field kit and, for comparison, by use of two known and approved laboratory test methods. The primary comparison test (referred to below as "Comparison Test 1") was a modification of ASTM Method D 808-63 (81), *Chlorine in New and Used Petroleum Products (Bomb Method)*. The ASTM method was modified by replacing the gravimetric finish with ion chromatography using a technique as reported by a Research Triangle Institute (RTI) study for the Federal Environmental Protection Agency (EPA). This EPA study is reported in A. Gaskill, Jr., and E. D. Estes, *Development and Validation of Sample Preparation and Analysis Procedures for Determination of Inorganic and Organic Chlorine and Other Halogen Species in Used and Waste Oils.* Final Report, EPA Contract No. 68-01-7075, Work Assignment No. 18, U.S. EPA, Office of Solid Waste, Nov. 1985. The second comparison test (referred to below as "Comparison Test 2") was a microcoulometric analytical method in which the hydrocarbon liquid sample is burned in a flowing gas stream and the evolved inorganic chlorine is passed to an aqueous medium wherein the halogen is titrated with electrically generated silver. This method was also found to be acceptable by RTI in a subsequent study for EPA, as reported in A. Gaskill, Jr., E. D. Estes, and D. L. Hardison, *Evaluation of Methods for Determining Chlorine in Used Oils,* Final Report, EPA Contract No 68-01-7075, Work Assignment No. 51, U.S. EPA, Office of Solid Waste, Aug. 1986.

Each of ASTM Method D-808-63(81) and the two EPA reports are incorporated by reference herein. Reference below to the "three test methods" is to Comparison Test 1, Comparison Test 2 and a Field Kit Test using the commercially available field test kit embodiment of the present invention, sold by Dexsil Corporation of Hamden, Conn., under its trademark CLOR-D-TECT as the CLOR-D-TECT 1000 disposable test kit for determining chlorine content in waste oil. In cases where solvents different from those of Example I were substituted, the data is reported under "Modified Field Test Kit". In some few cases, the data reported for a method and apparatus in accordance with the present invention shows specific ppm readings for the halides content instead of simply reporting greater than or less than 1000 ppm. Those cases are also reported under "Modified Field Test Kit" because use of the commercially available field test kit was modified by titrating to the endpoint instead of adding the pre-measured quantity of mercuric nitrate titrant. Both the technique of titrating to an endpoint and that of reacting a fixed quantity of titrant reagent lie within the purview of the present invention. Thus, the present invention also provides for adding a metered amount of titrant until a discernable end-point, e.g., a color change, formation of a precipitate or of turbidity, a change in electrical conductivity, etc., is noted. This titrating technique will indicate the actual ppm halogen, e.g., chlorine, in the tested sample and is not, like the field test kit embodiment of the present invention, limited to providing a "yes" or "no" indication as to whether or not a pre-selected level, e.g., 1000 ppm, of halogen exists in the tested sample. However, the field test kit embodiment of the apparatus of the present invention has the significant advantage of greatly simplifying the test and permitting accurate "yes" or "no" testing by untrained persons, even under adverse field conditions.

EXAMPLE I

The commercially available field test kit contains first and second test-tube shaped resilient containers and a sampling device substantially as illustrated in FIGS. 1 and 2 of the drawings, together with an absorbent tissue wipe for cleaning the exterior of the capillary sampling tube. The field test kit contains the following components.

| Corresponding Item of FIG. 2 | Component |
|---|---|
| 12 | Frangible glass capilliary tube, 102 mm long, OD/ID ratio = 1.1. |

| Corresponding Item of FIG. 2 | Component |
|---|---|
| | ID = 2.6 mm. (OD = outside diameter, ID = inside diameter). Volume of the interior of the tube is thus 0.542 ml. |
| 38 | Breakable glass ampule containing 70 mg of metallic sodium dispersed in mineral oil. |
| 40 | Breakable glass ampule containing 1.5 mls of a solvent comprised of 91% by weight of a mixture of 90% by volume diethylene glycol dibutyl ether and 10% by volume diethylene glycol diethyl ether; and 9% by weight naphthalene. On a weight percentage basis, this is 82% diethylene glycol dibutyl ether, 9% diethylene glycol diethyl ether and 9% naphthalene. |
| 54 | 7 mls of aqueous extractant liquid comprising an 8% solution of sodium sulfate, containing buffering agents to provide an analytical buffer, and 0.0112 g of cadmium sulfate. |
| 50 | Breakable glass ampule containing 0.75 ml of a standard mercuric nitrate aqueous solution. |
| 52 | Breakable glass ampule containing 0.5 mls of diphenylcarbazone indicator in ethanol. |

Actual ppm chlorine levels of a used oil were determined by using the reagent chemicals of the above-described field test kits and, for comparison, by Comparison Test 2. The actual ppm chlorine levels were determined by the reagents of the above-described field test kit by modifying the technique of the kit to carry out color change endpoint titrations instead of the fixed point titration provided by the pre-measured kit reagents. The results were compared to those obtained by Comparison Test 2, with the results shown in Example I.

EXAMPLE IA

The test kit of Example I, except that 1.1 ml of the following solvent is substituted for the solvent in item 40 of FIG. 2: 60 volume % mineral spirits (petroleum ether), 20 volume % butyl ether, 20 volume % toluene, and 0.4 mls of a 25% weight percent solution of naphthalene in diethylene glycol dimethyl ether (diglyme).

EXAMPLE II

Chlorine in the form of monochlorobenzene ("MCB"), 1-chlorooctadecane ("COD") or dichloromethane ("DCM") was added to samples of a used crankcase oil. The respective chlorine contents of the samples were determined by using the technique and chemicals of the present invention to carry out a mercuric ion color change titration ("Method Embodiment") and by the technique of Comparison Test 2. The following results were obtained:

| | Chlorine Content - ppm | |
|---|---|---|
| Type Of Additive | Field Test Kit | Comparison Test 1 |
| MCB | 969 | 885 |
| " | 1038 | 942 |
| " | 956 | 910 |
| COD | 1008 | 933 |
| " | 1047 | 1073 |
| DCM | 1054 | 960 |
| " | 1091 | 930 |
| " | 829 | 932 |
| " | 842 | 932 |

The results of Example II show that the technique and chemicals of one embodiment of the present invention provide good agreement with the results obtained by a laboratory analysis of established efficacy in determining chlorine content.

In the tests reported in the following Examples III–V, virgin and used oils were contaminated with various quantities of contaminant organic chlorine compounds, contaminant inorganic chlorine compounds and water. A volatile chlorinated organic compound, 1,1,1 trichloroethane (TCE), was used to simulate solvent contamination; trichlorobenzene (TCB) was used to simulate less volatile chlorinated solvents; 1-chlorooctadecane (COD) was used to simulate the high pressure-resistant additives sometimes found in metalworking oils, and sodium chloride (NaCl) was used to simulate inorganic chlorine compounds. These four contaminant compounds represent a wide variety of boiling point ranges and chemical properties, and are indicative of the capability of the measurement technique of the invention, even when embodied in a field test kit, to indicate whether or not a threshold level of chlorine is exceeded in a liquid hydrocarbon sample.

A comparison of the results obtained by the abovedescribed commercially available test kits in accordance with the present invention and the laboratory tests of Comparison Tests 1 and 2 are set forth in the following Examples III–V. The commercially available test kits use pre-measured, fixed quantities of reagent and therefore provide a fixed endpoint titration capable of showing, by a distinctive color or color change, whether or not a given quantity of chlorine (halogen) content is exceeded. With the chemicals used on the commercially available test kit, the diphenylcarbazone indicator will give a blue color for a sample chloride content of less than 1000 ppm and a yellow color for a sample chloride content greater than 1000 ppm.

EXAMPLE III

Various typical chlorinated contaminants were added to a virgin lubricating oil in the indicated amounts and analyzed by each of the three methods described. The results obtained were as follows:

| Added Chlorine | | Indicated Chlorine Content (ppm) | | |
|---|---|---|---|---|
| Quantity (ppm) | Type | Comparison Test 1 | Comparison Test 2 | Field Test Kit |
| 0 | — | 156 | 142 | <1000 |
| 500 | TCB | 544 | 552 | <1000 |
| 1140 | TCB | 1087 | 1113 | >1000 |
| 2123 | TCB | 2126 | 1973 | >1000 |
| 717 | TCE | 766 | 661 | <1000 |
| 1758 | TCE | 1639 | 1410 | >1000 |
| 1197 | TCE | 1094 | 937 | >1000 |
| 1610 | NaCl | 1596 | 1560 | >1000 |

The results tabulated in Example III show that the field test kit of the invention accurately identified the chlorine content of the test samples as being greater or less than 1000 ppm. The test results show that this essential information can be obtained by field tests using a kit in accordance with the present invention, without necessity of resorting to sophisticated laboratory procedures such as those of Comparison Test 1 and Comparison Test 2. Of course, the latter tests do provide specific ppm readings rather than simply indicating whether or not a specific threshold level such as 1000 ppm chlorine is attained. However, it should be noted that for the 1197 ppm chlorine sample, the field test kit of the invention accurately showed a reading of greater than 1000 ppm whereas Comparison Test 2 was some 260 ppm low.

EXAMPLE IV

Various typical chlorinated contaminants were added to a used crackcase oil in varying amounts and the resultant compositions were analyzed by each of the three methods described. The results obtained were as follows:

| Added Chlorine | | Indicated Chlorine Content (ppm) | | |
|---|---|---|---|---|
| Quantity (ppm) | Type | Comparison Test 1 | Comparison Test 2 | Field Test Kit |
| 0 | — | 734 | 739 | <1000 |
| 1816 | TCE | 1660 | 1517 | >1000 |
| 1225 | COD | 1104 | 1191 | >1000 |
| 2075 | COD | 1924 | 1993 | >1000 |
| 1475 | NaCl | 1394 | 1383 | >1000 |
| 1725 | NaCl | 1626 | 1787 | >1000 |

The data of Example IV show that the field test kit of the invention accurately indicated whether the chlorine content of used crankcase oil samples was greater or less than 1000 ppm in each known case, and showed agreement with both the laboratory tests in the undoctored sample.

EXAMPLE V

Virgin and used samples of a metalworking fluid of the emulsifiable type were analyzed by each of the three methods described, with the following results:

| | Indicated Chlorine Content (ppm) | | |
|---|---|---|---|
| Sample | Comparison Test 1 | Comparison Test 2 | Field Test Kit |
| Virgin | 5 | 5 | <1000 |
| Used | 1472 | 1235 | >1000 |

The results of Example V show that the test kit in accordance with the present invention appears to give good results with metal working fluids. However, large quantities of water, sometimes as high as 95%, contained in used metalworking fluids may adversely affect the accuracy of the test. Generally, hydrocarbon liquids to be tested should not contain more than about 20% by weight, preferably not more than 10% by weight, water.

EXAMPLE VI

Various chlorinated contaminants were added to different fuel oils and analyzed by each of the three methods described. The results obtained were as follows:

| Added Chlorine | | Indicated Chlorine Content (ppm) | | |
|---|---|---|---|---|
| Quantity (ppm) | Type | Comparison Test 1 | Comparison Test 2 | Field Test Kit |
| 0 (a) | — | 58 | 1.7 | <1000 |
| 1135 (a) | COD | 1087 | 1112 | >1000 |
| 0 (b) | — | 91 | 12 | <1000 |
| 1101 (b) | COD | 958 | 1020 | <1000 |

(a) No. 2 fuel oil
(b) No. 6 fuel oil

In testing fuel oils, the results of Example VI show that the field test kit of the invention accurately identified the chlorine content as being greater than 1000 ppm in the case of 1135 ppm chlorine addition and showed a content of less than 1000 ppm chlorine in the case of 1101 ppm chlorine addition to the No. 6 fuel oil. It should be noted that one of the laboratory tests (Comparison Test 1) also showed less than 1000 ppm (958 ppm) and Comparison Test 2 was also low, showing 1020 ppm.

EXAMPLE VII

Various chlorinated contaminants were added to a hydraulic fluid and analyzed by each of the three methods described. The results obtained were as follows:

| Added Chlorine | | Indicated Chlorine Content (ppm) | | |
|---|---|---|---|---|
| Quantity (ppm) | Type | Comparison Test 1 | Comparison Test 2 | Field Test Kit |
| 0 | — | <50 | 13.1 | <1000 |
| 7350 | TCE.COD | 7134 | 4987 | >1000 |
| 4027 | COD | 3903 | 4160 | >1000 |

The results of Example VII show that the field test kit of the invention accurately reflected the chlorine content as being greater than 1000 ppm for the known minimum chlorine content doctored hydraulic fluid sample, and was in agreement with the results of the laboratory tests on the undoctored sample.

A major concern in testing of used hydrocarbon liquids is the effect of impurities usually found in such materials, for example, in used crankcase oils which are often highly contaminated with materials such as chromium and lead ions. A concern was whether such ions would compete with the mercury titration used in one embodiment of the present invention. The following tests were run on used crankcase oils of various and unknown origin that were randomly taken from the field and analyzed for contaminant content. The samples were then tested for chlorine content by the silver titration method described above and by using the test kit in accordance with the present invention. The results obtained were as follows:

EXAMPLE VIII

| | Metal Ion Content* | | Indicated Chlorine Content* | |
|---|---|---|---|---|
| Sample | Cr | Pb | Comparison Test 2 | Field Test Kit |
| 1 | 40 | 14,900 | 2,270 | >1000 |
| 2 | 4 | 4,200 | 685 | <1000 |
| 3 | 3 | 1,150 | 6,340 | >1000 |
| 4 | 8 | 1,550 | 339 | <1000 |
| 5 | 2 | 1,300 | 433 | <1000 |
| 6 | 5 | 3,500 | 1,220 | >1000 |
| 7 | 3 | 3,100 | 1,225 | >1000 |

-continued

| | Metal Ion Content* | | Indicated Chlorine Content* | |
|---|---|---|---|---|
| Sample | Cr | Pb | Comparison Test 2 | Field Test Kit |
| 8 | 1 | 2,500 | 740 | <1000 |

*Measured in parts per million parts by weight

The data of Example VIII demonstrate consistent agreement concerning chlorine content between the field kit comprising one embodiment of the present invention, and the laboratory of Comparison Test 2 method. It also indicates that the test kit worked well with samples which are highly contaminated with metal ions which might be expected to compete with the mercuric ion titration used in the field test kit embodiment of the invention.

EXAMPLE IX

The following example compares results attained by Comparison Test 2 and a modified version of the field test kit of Example I in which in place of the Example I solvent there was substituted a mixture of 50% by volume mineral spirits (petroleum ether) and 50% by volume diethylene glycol diethyl ether (ethyl diglyme). Three different types of No. 6 fuel oils were tested for chloride content by using Comparison Test 2 and the field test kit of Example I, modified by substituting the above solvent and titrating to a fixed endpoint. The following results were obtained.

| Fuel Oil Sample | ppm Chloride by Comparison Test 2 | ppm Chloride by Modified Field Test Kit |
|---|---|---|
| A | 1065 | 1078 |
| B | 1090 | 1158 |
| C | 1650 | 1630 |

The foregoing Example IX shows that the data obtained by using a field test method and reagents of the present invention gives excellent agreement with the laboratory procedure of Comparison Test 2, even for No. 6 fuel oils.

EXAMPLE X

The method and reagents of the present invention as employed in Example X were utilized to test No. 6 fuel oil samples to which 1100 ppm halide had been added as, respectively, bromobenzene, iodobenzene and fluorobenzene.

| Material Added | Amount Added (ppm) | Amount Found (ppm) | % Rec. |
|---|---|---|---|
| Bromobenzene | 1100 | 1090 | 99 |
| Iodobenzene | 1100 | 1074 | 97 |
| Fluorobenzene | 1100 | 34 | 3 |

Example X shows the efficacy of the present invention in accurately analyzing for the halides bromide and iodide. Example X also illustrates that fluorides are not accurately analyzed by the use of a mercuric nitrate titrant when using the methods of the invention, because of the nonreactivity of mercuric nitrate with fluoride ions in solution.

The sampling technique of the present invention includes crushing the filled capillary tube so that the entire sample within the tube is available for analysis. The "breakability" of various commercially available ampules, capillary tubes and a glass pipette was tested, "breakability" being defined as the ease with which the article broke when squeezed between thumb and forefinger. The results obtained from the study are shown in the following Table, in which "ID" means inside diameter, "OD" means outside diameter and "Wall" means wall thickness of the article, and "OD/ID" means the ratio of the outside to the inside diameter of the article.

TABLE

| Article | Tube Dimensions (mm) | | | | Observation |
|---|---|---|---|---|---|
| | ID | Wall | OD | OD/ID | |
| 7 mm Ampule | 6.4 | 0.19 | 6.79 | 1.06 | Easily Breakable |
| 9 mm Ampule | 8.8 | 0.23 | 9.2 | 1.06 | Easily Breakable |
| Pipette | 1.1 | 0.11 | 1.3 | 1.18 | Extremely hard to break |
| Cap. Tube | 0.9 | 0.29 | 1.5 | 1.67 | Unbreakable |
| Cap. Tube | 2.6 | 0.2 | 3.0 | 1.15 | Breakable |
| Cap. Tube | 2.6 | 0.12 | 2.5 | 1.11 | Easily Breakable |
| Cap. Tube | 1.7 | 0.3 | 2.3 | 1.35 | Unbreakable |
| Cap. Tube | 2.8 | 0.2 | 3.2 | 1.14 | Breakable |

As can be seen, "breakability" is not a function simply of wall thickness but, rather, of the ratio of the outside diameter to the inside diameter ("OD/ID") which, obviously, must be greater than 1.0. Lower ratios of OD/ID indicate increased tube fragility and higher ratios indicate increased tube strength. For glass capillary tubes, OD/ID ratios of greater than about 1.06 but less than about 1.18 have been found to provide a capillary tube which is strong enough to be conveniently handled in assembly and use as contemplated by the invention without breaking, yet frangible enough to be easily broken, when desired, between thumb and forefinger while inside the resilient test container.

While the invention has been described in detail in connection with a specific embodiment thereof, variations to the illustrated embodiment lying within the spirit of the invention and the scope of the appended claims may become apparent to those skilled in the art upon a reading and understanding of the foregoing description.

What is claimed is:

1. An apparatus for testing liquids comprises a test kit containing the following components:
    (a) sampling means comprising (i) a frangible collector having an exterior and a collector interior of predetermined volume, the collector having therein (1) one opening leading from its exterior to its collector interior and defining a sampling end of the collector, and (2) another opening spaced from said one opening and leading from the exterior of the collector to its collector interior, said another opening defining a suction end of the collector; (ii) suction means having a suction port; and (iii) coupling means releasably connecting the suction end of the collector in flow communication with the suction port, whereby suitable suction applied to the suction end of the collector while the sampling end thereof is immersed in a hydrocarbon liquid will fill the collector with the liquid to provide a measured quantity of the liquid within the collector, and maintenance of such suction will retain the measured quantity of liquid within the collector;
    (b) a container system comprising at least a first container having an exterior, a container interior, and a container opening therein, the first container and the container opening being dimensioned and configured to enable the entire collector and the liquid contained therein to be inserted through the container opening and deposited within the first container from exteriorly thereof, at least a portion of the first container being sufficiently flexible to enable breaking of the frangible collector within the first container by squeezing the first container from the exterior thereof; and (c) one or more reagents stored in frangible segregating means which are dimensioned and configured to be stored within the container system, the reagents being of a quantity and type suitable for contacting the liquid within the container system and providing, in conjunction with the measured quantity of the liquids, a detectable indication of a characteristic of the liquid.

2. The apparatus of claim 1 wherein the collector is a frangible capillary tube.

3. The apparatus of claim 1 or claim 2 wherein the suction means comprises a syringe and the coupling means comprises a length of tubing having opposite ends, one of the opposite ends being connected to the suction port, and the tubing having an inside diameter sized to releasably receive therein, at the other of the opposite ends, the suction end of the capillary tube.

4. An apparatus for testing liquids comprises:

(a) sampling means comprising (i) a frangible collector comprising a frangible capillary tube of pre-determined interior volume, the capillary tube having an opening at one end thereof defining a sampling end of the capillary tube, and another opening at its opposite end defining a suction end of the capillary tube; (ii) suction means having a suction port; and (iii) coupling means releasably connecting the suction end of the capillary tube in flow communication with the suction port, whereby suitable suction applied to the suction end of the capillary tube while the sampling end thereof is immersed in a hydrocarbon liquid will fill the capillary tube with the liquid to provide a measured quantity of the liquid within the capillary tube and maintenance of such suction will retain the measured quantity of liquid within the capillary tube;

(b) a container system comprising at least a first container having an exterior, a container interior, and a container opening therein, the first container and the container opening being dimensioned and configured to enable the entire collector and the liquid contained therein to be inserted through the container opening and deposited within the first container from exteriorly thereof, at least a portion of the first container being sufficiently flexible to enable breaking of the capillary tube within the first container by squeezing the first container from the exterior thereof; and (c) one or more reagents stored in frangible segregating means disposed within the container system and being of a quantity and type suitable for contacting the liquid within the container system and providing, in conjunction with the measured quantity of the liquid, a detectable indication of a characteristic of the liquid.

5. The apparatus of claim 2 or claim 3 wherein the capillary tube is a glass tube having a ratio of outside diameter to inside diameter of about 1.06 to 1.18 and a wall thickness of from about 0.12 mm to 0.29 mm.

6. The apparatus of claim 1, claim 2 or claim 3 wherein the reagents are of a quantity and type selected to provide, in conjunction with the measured quantity of the hydrocarbon liquid, a detectable indication of the halogen content of the hydrocarbon liquid.

7. The apparatus of claim 6 wherein the reagents comprise a solvent for hydrocarbon liquids, an alkali metal reactant, an aqueous extractant liquid, a titrant for halides, and a color change indicator for the titrant reaction.

8. The apparatus of claim 7 wherein the solvent comprises diethylene glycol diethyl ether, diethylene glycol dibutyl ether and naphthalene, and the aqueous extractant comprises an aqueous solution of sodium sulfate, a mineral acid other than a hydrohalide acid, and sodium acid phosphate.

9. The apparatus of claim 7 wherein the aqueous extractant includes cadmium sulfate.

10. A method for measuring halogen content of a hydrocarbon liquid, the method comprising:

(a) taking a measured quantity sample of the hydrocarbon liquid by suctioning the liquid into a frangible collector having a pre-determined interior volume;

(b) depositing the collector containing the sample into a container from exteriorly thereof and breaking the collector within the container to release the liquid from the collector;

(c) contacting the liquid sample with one or more reagents to provide a reaction residue in the container, the quantity and type of reagents being selected to provide, in conjunction with the measured quantity of the liquid, a detectable indication of the halogen content of the liquid; and (d) observing the detectable indication.

11. The method of claim 10 wherein the collector comprises a frangible capillary tube.

12. The method of claim 10 or claim 11 including completely filling the collector with the sample and depositing the completely filled collector into the container.

13. The method of claim 10 or claim 11 including removing excess hydrocarbon liquid from the exterior of the collector prior to depositing the collector within the first container.

14. The method of claim 10 or claim 11 including contacting the liquid hydrocarbon sample with an alkali metal reagent to react the alkali metal reagent with any halogen materials in the sample in order to form inorganic halides therefrom; contacting the resultant reacted sample with an aqueous extractant which extracts the resultant inorganic halides and forms an aqueous phase which separates from a hydrocarbon phase; titrating the inorganic halides in the aqueous phase with a pre-measured quantity of a titrant; and contacting the titrated aqueous phase material with an indicator which acquires a characteristic color depending upon whether or not the quantity of inorganic halides present in the aqueous phase is sufficient to react with all of the added titrant, whereby the resultant color provides the detectable indication of whether or not a pre-selected level of halogen was present in the liquid hydrocarbon sample.

15. The method of claim 14 wherein the aqueous extractant comprises an aqueous solution including cadmium sulfate.

16. The method of claim 14 including, in step (b), dissolving the sample of hydrocarbon liquid in a solvent within the container.

17. The method of claim 16, wherein the solvent comprises diethylene glycol diethyl ether, diethylene glycol dibutyl ether and naphthalene, and the aqueous extractant comprises an aqueous solution of sodium sulfate, a mineral acid other than a hydrohalide acid, and sodium acid phosphate.

* * * * *

UNITED STATES PATENT AND TRADEMARK OFFICE
CERTIFICATE OF CORRECTION

PATENT NO. : 5,013,667

DATED : May 7, 1991

INVENTOR(S) : Lynn et al.

It is certified that error appears in the above-identified patent and that said Letters Patent is hereby corrected as shown below:

```
In column 5, line 50, "in to" should read --into--.
In column 7, lines 25-26, "napththalene" should read
    --naphthalene--.
In column 8, line 41, "gain" should read --again--.
In column 9, line 59, "titant" should read --titrant--.
In column 10, line 37, "flamability" should read --flammability--.
In column 14, line 33, there should be a hyphen between "above"
    and "described".
In column 15, line 55, "metal working" should be written as
    one word.
 In Col. 17, line 7, the footnote to the table heading "Metal Ion
    Content", which appears near the top of column 17, should
    have a comma after "million parts".
In claim 1, column 18, line 49, "predetermined" should read
    --pre-determined--; and in
            column 19, line 16, "liquids" should read --liquid--.
In claim 4, column 19, line 48, "collector" should read
    --capillary tube--.
Claim 5, column 19, line 62, should read --The apparatus of
    claim 2 or claim 4...--.
Claim 6, column 19, line 66, should read --The apparatus of
    claim 1, claim 2 or claim 4...--.
```

UNITED STATES PATENT AND TRADEMARK OFFICE
CERTIFICATE OF CORRECTION

PATENT NO. : 5,013,667

DATED : May 7, 1991

INVENTOR(S) : Lynn, et al

It is certified that error appears in the above-identified patent and that said Letters Patent is hereby corrected as shown below:

Claim 6, column 19, line 66, should read --The apparatus of claim 1, claim 2 or claim 4...--.

Signed and Sealed this

Sixth Day of April, 1993

*Attest:*

STEPHEN G. KUNIN

*Attesting Officer*       Acting Commissioner of Patents and Trademarks